United States Patent
Bauer et al.

(10) Patent No.: US 6,617,469 B2
(45) Date of Patent: Sep. 9, 2003

(54) PROCESS FOR PREPARING MALONIC DIESTERS IN A REACTOR WITH INTERNAL HEAT EXCHANGERS

(75) Inventors: Frank Bauer, Haltern (DE); Wilfried Latz, Troisdorf (DE); Uwe Prange, Niederkassel (DE); Christoph Theis, Niederkassel (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/726,556

(22) Filed: Dec. 1, 2000

(65) Prior Publication Data

US 2001/0018540 A1 Aug. 30, 2001

(30) Foreign Application Priority Data

Feb. 25, 2000 (DE) .......................... 100 08 903

(51) Int. Cl.⁷ .......................... C07C 69/34; C07C 69/76
(52) U.S. Cl. ................. 560/190; 560/100; 560/105; 560/102; 560/187; 560/204; 422/198; 422/201; 422/205; 422/224; 562/406
(58) Field of Search ................ 560/190, 105, 560/100, 102, 187, 204; 422/205, 201, 198, 224; 562/406

(56) References Cited

U.S. PATENT DOCUMENTS

| | | | | |
|---|---|---|---|---|
| 4,424,375 A | * | 1/1984 | El-Chahawi et al. | 560/105 |
| 5,478,535 A | * | 12/1995 | Fierz et al. | 422/205 |

FOREIGN PATENT DOCUMENTS

| | | |
|---|---|---|
| DE | 25 53 931 | 6/1977 |
| DE | 198 36 807 | 2/2000 |
| EP | 0 633 060 | 1/1995 |
| JP | 54112818 | 2/1978 |
| JP | 57183741 | 8/1978 |

* cited by examiner

*Primary Examiner*—Alan L. Rotman
*Assistant Examiner*—Hector M Reyes
(74) *Attorney, Agent, or Firm*—Oblon, Spivak, McClelland, Maier & Neustadt, P.C.

(57) ABSTRACT

A process for preparing malonic diesters by carbonylation of haloacetic esters and reaction with monohydric alcohols and a base in the presence of a transition metal catalyst, preferably a catalytic cobalt carbonyl complex, using a stirred reactor with one or more internal heat exchangers. The stirred reactor preferably contains a sparging stirrer.

13 Claims, No Drawings

PROCESS FOR PREPARING MALONIC DIESTERS IN A REACTOR WITH INTERNAL HEAT EXCHANGERS

The invention relates to a process for preparing malonic diesters by carbonylation of haloacetic esters, in particular alkyl chloroacetates, with carbon monoxide and reaction with monohydric alcohols and bases in the presence of transition metal catalysts using a reactor with one or more internal heat exchanger(s).

It is known that malonic diesters of the formula I

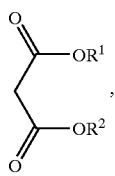

where $R^1$ and $R^2$ are each, independently of one another, an unbranched or branched alkyl or alkenyl group, a cycloalkyl group or an aralkyl group having from 1 to 30 carbon atoms, preferably an alkyl group having from 1 to 6 carbon atoms, can be prepared by carbonylation of haloacetic esters of the formula II

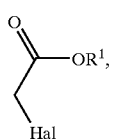

where $R^1$ is as defined above and Hal is a halogen atom, with carbon monoxide and reaction with a monohydric alcohol of the formula $R^2OH$, where $R^2$ is as defined above and preferably corresponds to the radical $R^1$ in formula II, using a base in the presence of a transition metal catalyst.

In the carbonylation of compounds of the formula II and reaction with monohydric alcohols, considerable heat of reaction is liberated. On an industrial scale, the reaction is therefore customarily carried out in a loop reactor such as a BUSS reactor (DE-A 25 53 931).

The yields of compounds of the formula I achieved are usually above 90% of theory, based on the amount of haloacetic ester used, even when the reaction is carried out on an industrial scale. With a view to minimizing the production costs, it is therefore particularly important to optimize the space-time yields. In principle, these can be improved by increasing the reaction temperature and increasing the starting material concentrations.

An increase in the reaction temperature is desirable not only because of the associated increase in the reaction rate, but also, in view of the highly exothermic nature of the reaction, because of the greater temperature difference between reaction medium and cooling medium.

However, an increase in the reaction temperature is subject to limits for a number of reasons. Thus, reaction temperatures significantly above 100° C. are not possible because the catalyst is then generally no longer stable even in the presence of high carbon monoxide partial pressures.

It is also known that the yield of malonic diesters, based on the amount of haloacetic esters reacted, drops with increasing reaction temperature. Thus, the isolated yields of the particularly important dimethyl malonate are from 2 to 3 percent lower when the reaction is carried out at 90° C. instead of at 50–70° C. under otherwise unchanged conditions. Conversely, reaction temperatures significantly below 90° C. are not acceptable on an industrial scale because of the considerable increases in the reaction times associated therewith (JP 57–183 741).

An increase in the starting material concentration is likewise subject to restrictions. Thus, the halides formed during the reaction are generally obtained as solid salts. The bases used are also frequently crystalline solids under the reaction conditions (for example sodium carbonate). The formation of salt leads, particularly together with the water formed during the reaction, at comparatively high starting material concentrations of, for example, 25% solids in the reaction mixture to this mixture no longer being able to be fully uniformly mixed when carrying out the reaction in a stirred reactor or a loop reactor or BUSS reactor. It has also been found that an increase in the content of, for example, alkyl chloroacetate and/or dialkyl malonate in the reaction mixture to over 3.75 mol/l of reaction volume is associated with a reduction in selectivity in conventional reactors.

Although it is possible to improve the selectivity of the carbonylation reaction by means of additives to the reaction mixture (JP 54 112 818), this can make the work-up of the reaction products more difficult. Contamination caused by additives is also a considerable disadvantage in respect of further utilization of the solvent(s), of the catalyst or of its downstream products and especially of the salt formed.

It is therefore an object of the invention to find a process for preparing malonic diesters of the formula I by carbonylation of haloacetic esters of the formula II with carbon monoxide and reaction with monohydric alcohols which does not have the abovementioned disadvantages and which gives improved space-time yields at simultaneously unimpaired or improved product selectivity.

It has now surprisingly been found that very high space-time yields can be achieved if the carbonylation reaction and reaction with the monohydric alcohol is carried out in a stirred reactor provided with one or more internal heat exchanger(s).

The invention accordingly provides a process for preparing malonic diesters of the formula I,

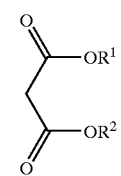

where $R^1$ and $R^2$ are each, independently of one another, an unbranched or branched alkyl or alkenyl group, a cycloalkyl group or an aralkyl group having from 1 to 30 carbon atoms, by carbonylation of haloacetic esters of the formula II,

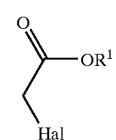

where $R^1$ is as defined above and Hal is a halogen atom, using carbon monoxide, a monohydric alcohol of the formula $R^2OH$, where $R^2$ is as defined above, a base and a transition metal catalyst, wherein the reaction is carried out in a stirred reactor with one or more internal heat exchanger(s).

In this way, for example, it was possible to use up to 5.2 mol of methyl chloroacetate per liter of liquid phase of the reaction mixture in the preparation of the industrially particularly important dimethyl malonate without mixing problems occurring. In addition, the yields of isolated target product (assay: >99.7%) achieved in this way were, for example, 92.0% and thus comparable with those obtained under analogous conditions but in greater dilution in the BUSS reactor (91.5%) or a stirred reactor (91.3%).

The components can be combined at ambient temperatures (room temperature). The reaction temperatures are from 40 to 100° C., preferably from 50 to 95° C. However, regardless of the type of reactor used, it has been found to be advantageous in terms of high space-time yields to approach desirable high reaction temperatures of, for example, 90° C. continuously via a defined temperature ramp. It has been found to be particularly advantageous to heat the reaction mixture initially to the temperature required for starting the reaction, for example 50° C., before then increasing the temperature stepwise or preferably continuously to, for example, 90° C. If desired, an afterreaction phase can follow at the same temperature level or a lower temperature level.

To enable good mixing of the carbon monoxide with the suspension comprising the remaining components of the reaction mixture in the case of the stirred reactor and the stirred reactor with one or more internal heat exchanger(s), the use of a sparging stirrer is advantageous. In this way, satisfactory dispersion of the carbon monoxide in the reaction mixture can be achieved even on an industrial scale without external pumps or compressors having to be used.

Surprisingly, it has also been found that deposits of the halide formed during the reaction can be largely avoided if a stirred reactor provided with sparging stirrer and internal heat exchangers as described in EP-A-0 633 060, hereinafter also referred to as a "BIAZZI" reactor, is employed.

With regard to the excellent mixing of the carbon monoxide with the other components of the reaction mixture in a loop reactor or "BUSS" reactor, it has also surprisingly been found when using a "BIAZZI" reactor for the carbonylation of the haloacetic esters and reaction with the monohydric alcohol that the catalyst is subject to a significantly lower decomposition rate at the same carbon monoxide partial pressure and the same temperature. This enables higher reaction temperatures to be achieved and/or a lower than usual amount of transition metal catalyst to be used, as a result of which the costs of recirculating the latter to the process are lower.

The halogen in the haloacetic ester is chlorine, bromine or iodine. Preference is given to using chloroacetic esters.

As transition metal catalysts, it is possible to use transition metal complexes or transition metal complex salts containing transition metals selected from the group consisting of cobalt, ruthenium, palladium and platinum. Cobalt is preferred as transition metal. As catalytic cobalt carbonyl complex, preference is given to using dicobalt octacarbonyl and species which can be generated therefrom, for example alkali metal salts, in particular sodium salts, of hydridocobalt carbonyl. As bases, it is possible to use, in particular, alkali metal and alkaline earth metal hydroxides, carbonates and hydrogencarbonates. The sodium compounds, in particular sodium carbonate, are preferred.

It has likewise surprisingly been round that the isolated yields of malonic diesters or the formula I and thus the selectivities achieved increase regardless of the type of reactor used if the reaction mixture comprises not only the haloacetic ester of the formula II, the monohydric alcohol of the formula $R^2OH$, the carbon monoxide, the base and the transition metal catalyst but also from 0.1 to 60% by weight, preferably from 5 to 40% by weight, particularly preferably from 10 to 30% by weight, in each case based on the total reaction mixture, of a nonpolar solvent which is inert under the reaction conditions (cosolvent). Toluene has been found to be a particularly advantageous cosolvent.

An increasing addition of toluene initially results in increasing isolated yields of the compounds of the formula I. However, one finally reaches a point of maximum selectivity above which the isolated yields of the compounds of the formula I drop sharply.

The Theological behavior of the reaction mixture displays similar trends to the isolated yields. While small additions of toluene have, as expected, a small influence on the rheology of the reaction mixture, additions of >60% of toluene, based on the total reaction mixture, when carrying out the reaction in a stirred reactor or in a loop reactor or a BUSS reactor lead to formation of the salt of reaction in an increasingly greasy, difficult-to-handle and difficult-to-mix form. Furthermore, deposits of the salt of reaction which can only be partly removed by rinsing with the alcohol or alcohol/cosolvent mixture used are formed.

Surprisingly, greater amounts of cosolvent can be present in the reaction mixture without the abovementioned problems occurring when the reaction is carried out in the "BIAZZI" reactor. These higher cosolvent contents are in turn surprisingly accompanied by higher isolated yields of the malonic diesters of the formula I and thus higher selectivities. Thus, higher isolated yields of, for example, up to 94.3% of theory of dimethyl malonate (assay: >99.8%) can be achieved when the carbonylation reactions and reactions with the monohydric alcohol are carried out in the "BIAZZI" reactor with addition of cosolvent, in particular toluene, despite increased starting material concentrations and the associated increase in the space-time yields.

After the reaction is complete, the catalyst is preferably decomposed by means of oxygen or an oxygen-containing gas.

A fundamental advantage of a stirred reactor, whether without or with one or more internal heat exchangers, compared to a loop reactor or "BUSS" reactor is the opportunity of depressurizing the gas phase in the reactor more rapidly. The amounts of carbon dioxide formed during the reaction which are dissolved in the reaction mixture cause strong foaming in the case of rapid depressurization, and this leads at small gas-liquid interfacial areas to entrainment of liquid and solid components of the reaction mixture.

Together with the above-described results on increasing the space-time yield of the process, significantly shortened cycle times are therefore obtained in the case of batchwise operation of the reactor, or higher throughputs in the case of continuous reactor operation are possible compared to the simple stirred reactor and the loop or "BUSS" reactor. According to the invention, the time for filling and emptying the "BIAZZI" reactor, for heating the reaction mixture to the commencement of carbon monoxide absorption and for the actual carbonylation reaction and reaction with the monohydric alcohol can thus be reduced to cycle times of significantly less than 120 minutes, preferably not more than 90 minutes.

Malonic diesters are versatile synthetic building blocks in organic chemistry, For example as intermediates in the synthesis of pharmaceuticals, plastics, crop protection agents, fragrances, flavors and dyes.

The following examples serve to illustrate the process of the invention, but do not restrict its field of application.

EXAMPLE 1

Preparation of Dimethyl Malonate (Comparative Example—Stirred Reactor)

A mixture of 542.2 g of methyl chloroacetate, 727.4 g of methanol, 293.1 g of sodium carbonate and 16.3 g of dicobalt octacarbonyl were placed in a 2 liter stirring autoclave while stirring at room temperature. The mixture was then heated stepwise under a carbon monoxide (CO) partial pressure of 25 bar to a final temperature of 92° C., with the temperature ramp being selected so that overheating of the reaction mixture was ruled out.

The reaction time, measured from the beginning of carbon monoxide absorption to the achievement of a methyl chloroacetate conversion of >99.7%, was 90 minutes.

After aqueous work-up of the reaction mixture, the yield of dimethyl malonate isolated was 91.3% of theory, based on the amount of methyl chloroacetate used. The dimethyl malonate prepared in this way had a purity determined by gas chromatography of >99.5%.

EXAMPLE 2

Preparation of Dimethyl Malonate (Comparative Example—"BUSS" Reactor)

The procedure of Example 1 was repeated, but the reactor used was a "BUSS" reactor. Due to the reactor principle, the reaction here had to be carried out on a larger scale than in Example 1.

The reaction time, measured from the beginning of carbon monoxide absorption to the achievement of a methyl chloroacetate conversion of >99.5%, was 150 minutes.

The yield of dimethyl malonate isolated was 91.5% of theory, based on the amount of methyl chloroacetate used. The dimethyl malonate prepared in this way had a purity determined by gas chromatography of >99.5%.

EXAMPLE 3

Preparation of Dimethyl Malonate Using a "BIAZZI" Reactor

The procedure of Example 1 was repeated, but the reactor used was a "BIAZZI" reactor. Due to the reactor principle, the reaction had to be carried out on a larger scale than in Example 1.

The reaction time, measured from the beginning of carbon monoxide absorption to the achievement of a methyl chloroacetate conversion of >99.7%, was 70 minutes.

The yield of dimethyl malonate isolated was 93.4% of theory, based on the amount of methyl chloroacetate used. The dimethyl malonate prepared in this way had a purity determined by gas chromatography of >99.8%.

EXAMPLE 4

Preparation of Dimethyl Malonate ("BIAZZI" Reactor)

The procedure of Example 3 was repeated, but the amount of methyl chloroacetate used was increased to 4.8 mol per liter of reaction volume. In addition, a toluene content of the reaction mixture of 17.1% by weight was set.

The total time for filling and emptying the reactor together with the actual reaction time, measured from the beginning of carbon monoxide absorption to the achievement of a methyl chloroacetate conversion of >99.8%, was 90 minutes. The reaction product obtained after the reaction was complete contained the salt of reaction in readily dispersible, not at all greasy form. Salt of reaction adhering to the reactor walls could, even after a number of experiments, be completely removed without problems by rinsing with a methanol/toluene mixture.

The yield of dimethyl malonate isolated was 92.0% of theory, based on the amount of methyl chloroacetate used. The dimethyl malonate prepared in this way had a purity determined by gas chromatography of >99.8%.

EXAMPLE 5

Preparation of Dimethyl Malonate (Stirred Reactor) (Comparative Example)

The procedure of Example 4 was repeated, but the reactor used was a simple stirred reactor.

The reaction product obtained after the reaction was complete contained the salt of reaction in greasy, difficult-to-handle form. Salt of reaction adhering to the reactor walls could no longer be completely removed by rinsing with methanol or a methanol/toluene mixture after a number of experiments.

The yield of dimethyl malonate isolated was only 87% of theory, based on the amount of methyl chloroacetate used. The dimethyl malonate prepared in this way had a purity determined by gas chromatography of >99%.

What is claimed is:

1. In a process for preparing malonic diesters represented by formula I by carbonylation:

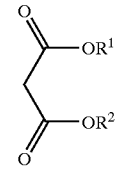

wherein
$R^1$ and $R^2$ are each, independently of one another, an unbranched or branched alkyl or alkenyl group, a cycloalkyl group or an aralkyl group having from 1 to 30 carbon atoms, comprising:
reacting a haloacetic ester represented by formula II:

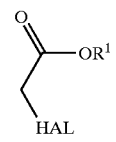

wherein
$R^1$ is as defined above; and
Hal is a halogen atom,
with carbon monoxide, a monohydric alcohol represented by the formula $R^2OH$, wherein $R^2$ is as defined above, and a base, in the presence of a transition metal complex or salt thereof catalyst,
the improvement comprising wherein the reaction is carried out in a stirred reactor having at least one internal heat exchanger.

2. The process of claim 1, wherein the stirred reactor contains a sparging stirrer.

3. The process of claim 1, wherein the reaction temperature is increased from an initial temperature to a final temperature by a preselected temperature ramp.

4. The process of claim 1, wherein the reaction mixture further comprises from 0.1 to 60% by weight of a nonpolar solvent which is inert under the reaction conditions.

5. The process of claim 4, wherein the nonpolar solvent is toluene.

6. The process of claim 1, wherein the reaction time, as measured from the beginning of carbon monoxide absorption to the achievement of a haloacetic ester conversion of >99.8%, is not more than 90 minutes.

7. The process of claim 1, wherein the haloacetic ester is a chloroacetic ester.

8. The process of claim 1, further comprising decomposing the transition metal complex or salt thereof catalyst with oxygen or an oxygen-containing gas.

9. The process of claim 1, wherein the transition metal of the transition metal complex or salt thereof catalyst is selected from the group consisting of cobalt, ruthenium, platinum and palladium.

10. The process of claim 9, wherein the transition metal is cobalt.

11. The process of claim 10, wherein the transition metal complex catalyst is dicobalt octacarbonyl.

12. The process of claim 1, wherein the base is selected from the group consisting of alkali metal hydroxides, alkaline earth metal hydroxides, alkali metal carbonates, alkaline earth metal carbonates, alkali metal hydrogen carbonates, and alkaline earth metal hydrogen carbonates.

13. The process of claim 1, wherein $R_1$ is methyl.

* * * * *